United States Patent
Law et al.

(10) Patent No.: US 8,883,083 B2
(45) Date of Patent: Nov. 11, 2014

(54) AIR CLEANER FILTER SYSTEM CAPABLE OF NANO-CONFINED CATALYTIC OXIDATION

(75) Inventors: Kwok Yung Anthony Law, Hong Kong (CN); Yu Hang Christopher Chao, Hong Kong (CN); Sui Chun Law, Hong Kong (CN); Wan Chung Lam, Hong Kong (CN)

(73) Assignee: RHT Limited, Hong Kong (CN)

( * ) Notice: Subject to any disclaimer, the term of this patent is extended or adjusted under 35 U.S.C. 154(b) by 0 days.

(21) Appl. No.: 10/512,368

(22) PCT Filed: Apr. 29, 2002

(86) PCT No.: PCT/CN02/00303
§ 371 (c)(1),
(2), (4) Date: Oct. 25, 2004

(87) PCT Pub. No.: WO03/093734
PCT Pub. Date: Nov. 13, 2003

(65) Prior Publication Data
US 2006/0024217 A1     Feb. 2, 2006

(51) Int. Cl.
*B01J 19/08*     (2006.01)
*B01D 53/04*     (2006.01)
(Continued)

(52) U.S. Cl.
CPC ........ *B01D 53/0438* (2013.01); *B01D 2257/80* (2013.01); *B01D 2253/10* (2013.01);
(Continued)

(58) Field of Classification Search
CPC .............. A61L 9/16; A61L 9/122; A61L 9/22; B01D 53/04; B01D 53/048; B01D 53/78; B01D 53/885

USPC ................ 422/186, 186.03, 186.04; 204/164; 250/423 R
See application file for complete search history.

(56) References Cited

U.S. PATENT DOCUMENTS

| 4,244,937 A | 1/1981 | Durkin |
| 4,673,416 A * | 6/1987 | Sakakibara et al. .............. 96/79 |

(Continued)

FOREIGN PATENT DOCUMENTS

| CN | 2317432 Y | 5/1999 |
| CN | 1275436 A | 12/2000 |

(Continued)

OTHER PUBLICATIONS

Jens Weitkamp, "Zeolites and catalysis", Solid State Ionics, 131 (2000) 175-188.*

(Continued)

*Primary Examiner* — Xiuyu Tai
(74) *Attorney, Agent, or Firm* — Eagle IP Limited; Jacqueline C. Lui

(57) ABSTRACT

The present invention is an air cleaner that uses molecular sieves, such as zeolite or other microporous/nanoporous crystalline materials with pore sizes ranging from 4 Å to 20 Å, as a filter to remove contaminant gas. The contaminants are adsorbed into the porous material along with ions clusters, or any other oxidant generated by a generating device within the system. The contaminant gas is then catalytically decomposed in the confined space of the pore. In one embodiment, transition metal is incorporated into the porous material, and a heater is installed to substitute or accompany the oxidant-generating device. When the heater is turned on, the contaminant is decomposed within the pores of the materials with the transition metals acting as catalysts. Ultimately, the non-harmful byproducts are the small sized water molecutes and carbon dioxide molecules. Growth of bacteria is also suppressed under a clean and dry condition.

10 Claims, 2 Drawing Sheets

(51) Int. Cl.
B01D 53/88 (2006.01)
B01D 53/86 (2006.01)
A61L 9/22 (2006.01)
B01D 53/78 (2006.01)
A61L 9/12 (2006.01)
A61L 9/015 (2006.01)
A61L 9/16 (2006.01)
F24F 3/16 (2006.01)

(52) U.S. Cl.
CPC ....... F24F 2003/1682 (2013.01); B01D 53/885 (2013.01); B01D 2257/91 (2013.01); B01D 53/86 (2013.01); F24F 2003/1628 (2013.01); A61L 9/22 (2013.01); Y02C 10/08 (2013.01); B01D 53/78 (2013.01); B01D 2253/108 (2013.01); F24F 3/166 (2013.01); B01D 2259/4508 (2013.01); B01D 53/04 (2013.01); B01D 2253/308 (2013.01); B01D 2257/504 (2013.01); A61L 9/122 (2013.01); A61L 9/015 (2013.01); A61L 9/16 (2013.01)
USPC ................ 422/186.04; 422/186; 422/186.03; 204/164; 204/250; 204/423 R

(56) References Cited

U.S. PATENT DOCUMENTS

| | | | | |
|---|---|---|---|---|
| 4,772,297 | A | * | 9/1988 | Anzai ................ 96/19 |
| 4,780,277 | A | * | 10/1988 | Tanaka et al. .......... 422/4 |
| 4,872,083 | A | | 10/1989 | Blitshteyn |
| 5,141,906 | A | * | 8/1992 | Takeshima et al. ...... 502/62 |
| 5,221,520 | A | | 6/1993 | Cornwell |
| 5,388,177 | A | * | 2/1995 | Ono et al. ............ 392/386 |
| 5,622,630 | A | * | 4/1997 | Romano ............. 210/683 |
| 5,685,895 | A | * | 11/1997 | Hagiwara et al. ......... 96/117 |
| 5,702,507 | A | | 12/1997 | Wang ................ 96/55 |
| 5,835,840 | A | | 11/1998 | Goswami .......... 422/186.3 |
| 5,843,288 | A | | 12/1998 | Yamamoto |
| 5,885,546 | A | * | 3/1999 | Kumar et al. .......... 423/703 |
| 5,939,028 | A | | 8/1999 | Bennett et al. |
| 5,961,919 | A | * | 10/1999 | Tachibana et al. ............ 422/3 |
| 6,120,584 | A | * | 9/2000 | Sakata et al. ........... 96/135 |
| 6,152,996 | A | * | 11/2000 | Linnersten et al. ........ 96/135 |
| 6,162,996 | A | | 12/2000 | Schmidt et al. ......... 174/259 |
| 6,299,854 | B1 | | 10/2001 | Henmi et al. ......... 423/700 |
| 6,358,374 | B1 | | 3/2002 | Obee et al. ......... 204/157.3 |
| 6,489,259 | B2 | * | 12/2002 | LaBarge et al. ........... 502/64 |
| 6,607,702 | B1 | | 8/2003 | Kang et al. ......... 422/186.3 |
| 6,887,438 | B2 | * | 5/2005 | Labarge et al. ............ 422/177 |
| 2002/0014071 | A1 | * | 2/2002 | Balmer et al. ............ 60/273 |
| 2002/0157661 | A1 | | 10/2002 | Kornberger |
| 2003/0030374 | A1 | * | 2/2003 | Pai ............... 313/582 |

FOREIGN PATENT DOCUMENTS

| | | |
|---|---|---|
| CN | 1340679 A | 3/2002 |
| EP | 0616175 A2 | 9/1994 |
| EP | 0950800 A2 | 10/1999 |
| EP | 1905458 A2 | 4/2008 |
| JP | 54-104481 A | 8/1979 |
| JP | 6-327922 A | 11/1994 |
| JP | 11-137658 A | 5/1999 |
| JP | 11-221442 A | 8/1999 |
| JP | 2001-246227 A | 9/2001 |
| RU | 1623346 A3 | 5/1998 |

OTHER PUBLICATIONS

Leighsenring et al "catalytic oxidation of chloraaromatic trace contaminants adsorbed on wessalith day by ozone", vol. 33 (1996), p. 343-352.*

S. E. Sen, S. M. Smith, and K. A. Sullivan, Organic transformations using zeolites and zeotype materials, Tetrahedron, 55 (1999) 12657-12698.

Thomas JM, Raja R, Sankar G, Bell RG. Molecular-sieve catalysts for the selective oxidation of linear alkanes by molecular oxygen. Nature, 1999, 398: 227-230.

* cited by examiner

Direction of airflow

Direction of airflow

US 8,883,083 B2

AIR CLEANER FILTER SYSTEM CAPABLE OF NANO-CONFINED CATALYTIC OXIDATION

TECHNICAL FIELD

This invention relates to the field of air cleaners, particularly air cleaners that adsorb gaseous contaminants. More specifically this invention relates to air-cleaners that are continuously self-regenerating and can decompose and permanently remove the filtered contaminants.

BACKGROUND ART

The problem of poor indoor air quality is found to be the cause of many health hazards, especially in modern domestic and commercial buildings where volatile organic compounds, nitrous oxide, ozone, and etc. are released by interior furnishing material as well as by human activities. Ventilation is not necessarily an adequate solution because outdoor air may be problematic as well. In addition, the energy load on the air-conditioning system is greater once outdoor air is used to ventilate the indoor space.

Common air-cleaners typically use activated carbon as a gas adsorbent. However, activated carbon filters tend to be expensive and must be periodically disposed of and replaced. The heterogeneously porous structure of activated carbon leads to competitive adsorption between water vapor and organic compounds, and eventually reduces its removal effectiveness. Moreover, heat generated from the adsorption process causes polymerization of the structure, and this degrading of the activated carbon structure further decreases the adsorption performance. Additionally, activate carbon is thermally unstable, high temperature regeneration is impractical and unsafe to do outside of a laboratory. As with most adsorption methods, the contaminant is not destroyed but merely transferred from the air onto the filter medium. This can lead to messy and dangerous cleaning processes. Prior inventions, such as that disclosed in U.S. Pat. No. 5,827,355, present a system with built-in regenerative processes of a carbon fiber composite molecular sieve by applying electrical currents to the filter medium. However, this process requires higher temperatures than those needed for zeolite regeneration. Additionally, the heating regeneration process periodically purges the filter of the contaminants and releases them back into the atmosphere. The present invention has the advantage of continuously decomposing the contaminant on the filter.

Photo-catalytic air-cleaners, such as that disclosed in U.S. Pat. No. 5,835,840, are also available and have the advantages of permanently removing the contaminants and having low maintenance and operating costs. However, when used unaccompanied by another device these systems are found to be slow acting and often produce imperceptible effects. U.S. Pat. No. 6,358,374 B1 discloses a system that integrates photo-catalytic technologies and adsorbent technologies. However, this system has a cumbersome method of periodically heating the adsorbent material, which releases a concentrated form of the contaminant into a chamber where the photo-catalytic mechanism is then applied. If there were a malfunctioning or leakage, it seems that this chamber of concentrated contaminants could become dangerous, depending on the type of contaminant contained within. Also, a substantial amount of contaminant must typically be absorbed before the system is regenerated. The preferred embodiment of the present invention has the advantage of being continuously self-regenerative without the use of the heater. In embodiments where the heater is employed the contaminants are decomposed during the heating process, unlike prior inventions. Additionally, in the present invention the contaminants remain secured on the zeolite until they are oxidized, a much less cumbersome and safer method.

Ion cluster emitting devices are also available, but have been found to act weakly on chemical pollutants. Charged ions clusters are generally effective in killing bacteria in the air, and decomposing certain odorous gases. However, an ion generator alone is ineffective in completely cleaning the air because the chance of charged ion cluster interacting with the contaminant gas molecule or bacteria is quite small. Moreover, charged ions clusters tend to react with the oxygen in the air to produce ozone, which in high concentrations is hazardous to human health. U.S. Pat. No. 5,702,507 discloses an invention that employs an ozone generator to destroy bacteria in the air. However, particularly in areas of low contaminant concentration, if the production of ozone is not carefully controlled, the growing levels of ozone could in fact create a worse indoor air quality level than that prior to employing the air cleaner. The present invention has the advantage of providing an inherent mechanism to eliminate the release of ozone.

Molecular sieves, such as zeolite or other crystalline zeolite complementary materials have a high porosity, and are effective in trapping contaminant gas molecules. Synthetic zeolite, unlike activated carbon, exhibits selectivity on adsorbed contaminants depending upon the shape, orientation, size hydrophilicity and chemical nature of the pores in zeolite. This allows specific filters to be developed to adsorb specific pollutants, increasing efficiency of an individual filter. Zeolite is also inexpensively produced, compared to activated carbon. Additionally, artificial zeolite production is environmentally friendly and takes advantage of unused resources, such as pyroclastic materials, inceration ash, waste glass, waste diatomaceous earth, and aluminum dross. A method for producing artificial zeolite is disclosed in U.S. Pat. No. 6,299,854 B1.

The thermal characteristics of zeolite make regeneration possible. At ambient temperatures, contaminant gas is adsorbed by zeolite because of the high porosity of zeolite crystallization and the weak polarity of zeolite molecules. When exposed to temperature above 45° C. temperature, the adsorbed gas molecules starting to release back to atmosphere. In a system where zeolite is used alone, without a regeneration device, the contaminants are merely secured until regeneration can occur. The contaminants are then released upon regeneration. The present invention is a system that takes advantage of zeolite's superior ability to adsorb pollutants, while also incorporating the technology of catalytic oxidation inside the pores of it.

DISCLOSURE OF THE INVENTION

The present invention has the principal object of providing an air cleaner which removes gaseous contaminants from the air of an indoor space.

The present invention has the further object of providing a continuously regenerating filter element that is semi-permanent.

The present invention has the further object of decomposing and permanently removing the gaseous contaminants from the confined space in the filter medium.

The present invention has the further object of controlling the amount of ozone released from the system.

The present invention has the further object of providing a less expensive, safer, and more environmentally friendly maintenance and operating procedure.

The present invention provides an alternate design to common air-cleaners, in which the gaseous pollutant together with the oxidant, which is generated by an oxidant-generating device, is adsorbed into the cavities of a microporous and/or nanoporous material, such as zeolite. The microporous/nanoporous material secures the adsorbed contaminant and oxidant into a confined space, thereby improving the efficiency of the charged ions at decomposing the contaminant by mean of oxidation. Since the ions continuously decompose the contaminants within the microporous/nanoporous materials, the microporous/nanoporous materials are continuously regenerated. A heater can be included or substituted into the system to more quickly decompose the contaminants from a molecular sieve that has transition metal incorporated into its structure.

BEST MODE FOR CARRYING OUT THE INVENTION

Figure 1:
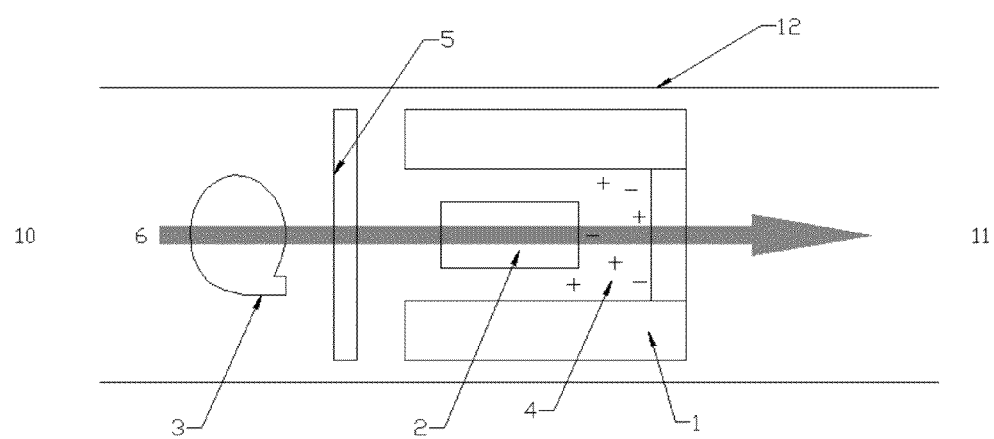
FIG. 1 Air cleaner system of ionizer and zeolite filter
Figure 2:
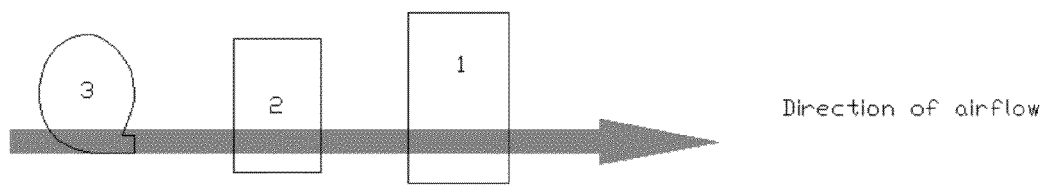
FIG. 2 Schematic diagram for air cleaner system arrangement 1
Figure 3:
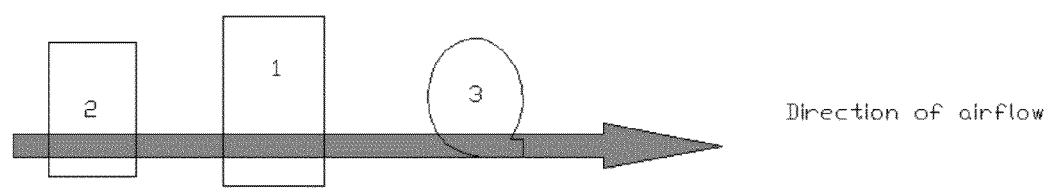
FIG. 3 Schematic diagram for air cleaner system arrangement 2

In one embodiment (FIG. 1), the present invention includes zeolite pellets with size varies from 2-6 mm, in either granular or cylinder form is packed into a porous enclosure (1) with an ionizer (2) fitted in the middle. Air is drawn into the middle hollow area by a fan/blower (3) and then forced through the zeolite filter while carrying charged ions (4). As shown, a housing (12) has an air entrance (10) and air exit (11). The system is airtight with the exception of the entrance area and exit area. A UPLA filter (5) is fitted at the entrance area in order to pre-treat the incoming air (6) and prevent large particles of dust in the incoming air from interfering with the effectiveness of the other devices, or igniting in the high temperatures of the electrical circuits. In the embodiment, the arrangement of the fan, zeolite, and ionizer can be modified to any arrangement such that the ionizer is placed before the zeolite filter. The zeolite filter could be at thickness from 0.5 inch to 3 inch depends on the area to be treated. The fan/blower with velocity varies from 0.005-0.1 m/s may be fitted before the ionizer and zeolite in order to blow the contaminated air together with the ions into zeolite filter (FIG. 2). A fan may also be fitted at the back of the zeolite filter and draw air from the ion generator into the zeolite filter (FIG. 3).

Once air enters the enclosure (1) it is bombarded with ions generated from the AC 30-60 kV ion generator (2), which will provide both positively and negatively charged ions (4). At this stage in the present invention's air filtration process, the released ions will already begin killing the bacteria and some of the pollutant gases in the air. Then the ions, along with the still contaminated air, flow into the zeolite enclosure.

The porous enclosure (1) used for holding the zeolite should be made of plastic or another insulating material that is not electrically charged by the passing ions. The pore size of the zeolite should range from 4 Å to 20 Å depending on the size of the contaminant and the oxidant. If the pore size is too large the zeolite cannot adsorb both the contaminants and oxidants. If the pore size of zeolite is too small, it can only hold either the contaminant or the oxidant, and the captioned oxidation reaction cannot be carried out. The type and size of the zeolite used are determined after evaluation tests (IAQ analysis) are performed to establish which contaminant is present in the specific indoor air space. Hydrophilic zeolite are used for an environment in which polar contaminants such as formaldehyde, alkanol, methylene choride are dominant. Hydrophobic zeolite is employed in environments where non-polar contaminants, such as toluene, benzene, aliphatic hydrocarbon are dominant. The zeolite pores secure the contaminant and provide an active site in which the ions, produced from the ion generator, can more effectively react with the contaminant. Thus, this invention is superior to mere zeolite filters, where the zeolite is just used to catch the contaminants, because the ions continuously regenerate the zeolite and result in a semi-permanent air filter.

In another embodiment, an ozone generator of 6 kV or above may be used in place of ionizer. Ozone performs the same catalytic oxidation reaction as ion generator. A percentage of zeolite with suitable pore size will be included in the batch to adsorb the excessive ozone, and provide an inherent method to control excess ozone. As an additional safety feature, an ozone sensor may be installed into the embodiment to monitor the ozone level. Once the ozone level reaches an unsatisfactory level, the ozone generator will stop generating ozone.

Figure 4:
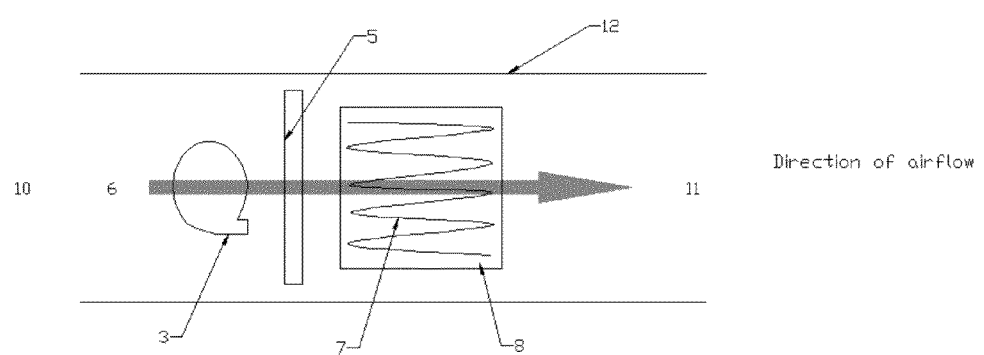
FIG. 4 Schematic air cleaner system arrangement according to claim 4

In another embodiment (FIG. 4), crystalline microporous/nanoporous materials with pore sizes complementary to zeolite is used in combination with or in substitution of the zeolite. The microporous/nanoporous materials may be metal oxide frameworks consisting of transition metals. In the device, a heater with 200W or above (7) is embedded in the metal oxide/complementary zeolite media. The porous enclosure (8) holding the metal oxide/complementary zeolite media should be made of metal or materials that are thermally stable. The contaminant is adsorbed on the metal oxide/complementary zeolite media, and the internal heater can be turned with temperature above 45° C. on and off as desired to provide a periodic regeneration. The transition metals incorporated in the microporous/nanoporous oxide frameworks will act as catalysts for oxidation of the contaminants in the pore. As with the previous embodiments, the byproducts of the regeneration process are non-harmful molecules, such as $H_2O$ and $CO_2$. In addition, the option of turning the heater off in an air-conditioned room is favorable to conserving energy.

Figure 5:
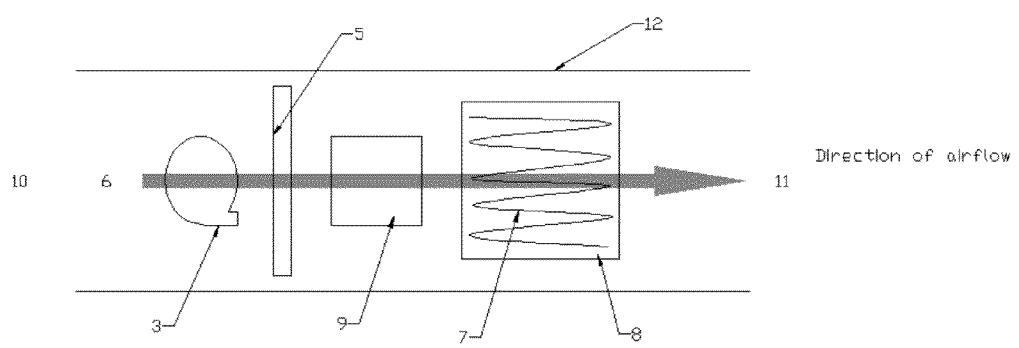
FIG. 5 Schematic air cleaner arrangement according to claim 4

In a further embodiment of the invention (FIG. 5), both the oxidant-generating device (9) and heater with 200 W or above (7) are used to optimize the regeneration process. The oxidant-generating device can provide cleaning and continuous regeneration of the zeolite or microporous/nanoporous metal oxide or complementary zeolite filter, while the heater can be turned on when ventilation is possible and a more thorough purging of the zeolite is desired.

The invention claimed is:

1. An air cleaner for catalytic oxidation of contaminant gasses comprising:
   a housing defining an enclosure and having an air entrance and an air exit;
   a pre-filter positioned to filter air entering said enclosure through said air entrance;
   a crystalline microporous/nanoporous filter within said enclosure, the crystalline microporous/nanoporous filter comprising filter material held in a filter enclosure that is an electrical insulator;
   an oxidant generating device for promoting catalytic oxidation of gaseous contaminants on said crystalline microporous/nanoporous filter wherein the oxidant generating device comprises an ion generator positioned in said stream of air upstream from said filter and said ion generator comprises an AC 30-60 kV ion generator which provides both positively and negatively charged ions to assist in the decomposition of said gaseous contaminants on said filter; and a blower arranged to generate a flow of air through said pre-filter and said crystalline microporous/nanoporous filter, wherein, the oxidant generating device is placed before the crystalline microporous/nanoporous filter along the direction of said flow of air, so that after said flow of air passes through the oxidant generating device, contaminant gasses in said flow of air and the oxidants from said oxidant generating device are directly and simultaneously adsorbed into the pores of said crystalline microporous/nanoporous filter, initiating break down of the contaminant gases with the pores of the filter by catalytic oxidation reaction with the oxidants generated from said oxidant generating device selectively at ambient temperature, in such a way contaminant gasses is simultaneously adsorbed and decomposed, and the microporous/nanoporous filter is continuously regenerated.

2. The air cleaner of claim 1, wherein said filter material comprises:

zeolite having a pore size in the range of 4 Angstroms to 20 Angstroms.

3. The air cleaner of claim 2, wherein filter material comprises:

a metal oxide framework constructed from materials including transition metals.

4. The air cleaner of claim 2, wherein said zeolite filter comprises:

granular or cylindrical zeolite pellets and said filter enclosure is porous in structure.

5. The air cleaner of claim 1, wherein said filter comprises filter material that has a pore size selected to permit adsorption of both the contaminant gas and an oxidant by said crystalline microporous/nanoporous filter.

6. The air cleaner of claim 2, wherein said zeolite filter comprises hydrophilic zeolite.

7. The air cleaner of claim 2, wherein said zeolite filter comprises hydrophobic zeolite.

8. The air cleaner of claim 1, wherein said pre-filter is an ultra low penetration air (ULPA) filter.

9. The air cleaner of claim 3 further comprising a heater arranged to heat said filter.

10. The air cleaner of claim 4, wherein said zeolite pellets are in cylindrical shape.

* * * * *